United States Patent [19]

Jeensalute et al.

[11] Patent Number: 4,565,500
[45] Date of Patent: Jan. 21, 1986

[54] AIR BUBBLE DETECTING AND DISCRIMINATING CIRCUIT ARRANGEMENT AND METHOD

[75] Inventors: Thipthep Jeensalute; Somkiat Chakkaw, both of Van Nuys, Calif.

[73] Assignee: Stewart-Riess Laboratories, Inc., Tarzana, Calif.

[21] Appl. No.: 469,412

[22] Filed: Feb. 24, 1983

[51] Int. Cl.[4] ................ F04B 21/00; F04B 43/12; A61M 5/00; G08B 21/00
[52] U.S. Cl. ........................... 417/53; 417/63; 417/412; 417/477; 604/67; 604/123; 604/153; 128/DIG. 13; 340/632
[58] Field of Search ............... 417/12, 45, 53, 63, 417/474–477, 412; 604/65, 67, 123, 153, 245; 128/DIG. 12, DIG. 13; 340/632

[56] References Cited

U.S. PATENT DOCUMENTS

| | | | |
|---|---|---|---|
| 3,731,679 | 5/1973 | Wilhelmson et al. | 417/45 X |
| 3,898,637 | 8/1975 | Wolstenholme | 604/123 X |
| 3,935,876 | 2/1976 | Massie et al. | 128/DIG. 13 X |
| 3,974,681 | 8/1976 | Namery | 128/DIG. 13 X |
| 4,114,144 | 9/1978 | Hyman | 604/123 X |
| 4,213,454 | 7/1980 | Shim | 604/123 X |
| 4,256,437 | 3/1981 | Brown | 417/63 X |
| 4,280,495 | 7/1981 | Lampert | 604/123 X |
| 4,312,341 | 1/1982 | Zissimopoulos et al. | 604/67 |
| 4,367,736 | 1/1983 | Gupton | 604/67 |
| 4,373,525 | 2/1983 | Kobayashi | 417/63 X |

OTHER PUBLICATIONS

Bigbie, et al., "Bubble Detector for Blood Circulating Devices," IBM Tech. Disclosure Bulletin, vol. 19, No. 3, pp. 769–771, Aug. 1976.

*Primary Examiner*—William L. Freeh
*Assistant Examiner*—Paul F. Neils
*Attorney, Agent, or Firm*—Flehr, Hohbach, Test, Albritton & Herbert

[57] ABSTRACT

An air bubble detecting and discriminating circuit arrangement especially suitable for use in a peristaltic infusion pump assembly is disclosed herein. This arrangement not only detects air bubbles in the fluid flowing through the tubing forming part of the assembly, but distinguishes between those bubbles which are sufficiently large to create a problem and smaller, micro bubbles which need not be detected. The arrangement also automatically compensates for changes in the flow rate of the fluid through the pump assemblies tubing without requiring any modifications at the time the flow rate is changed.

8 Claims, 5 Drawing Figures

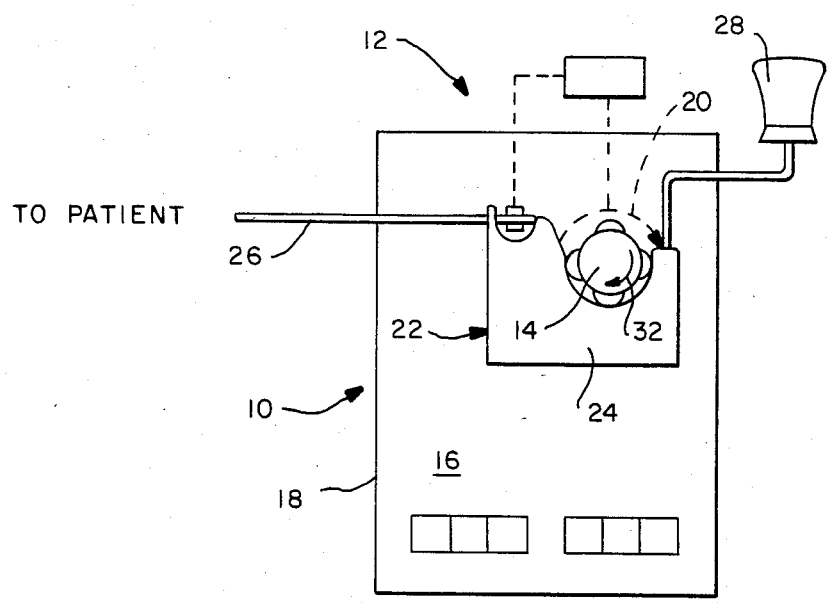
FIG.—1
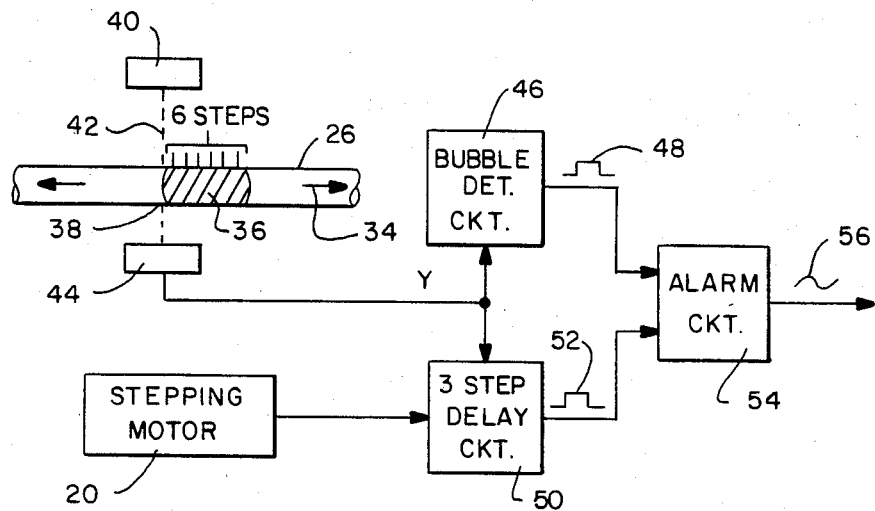
FIG.—2

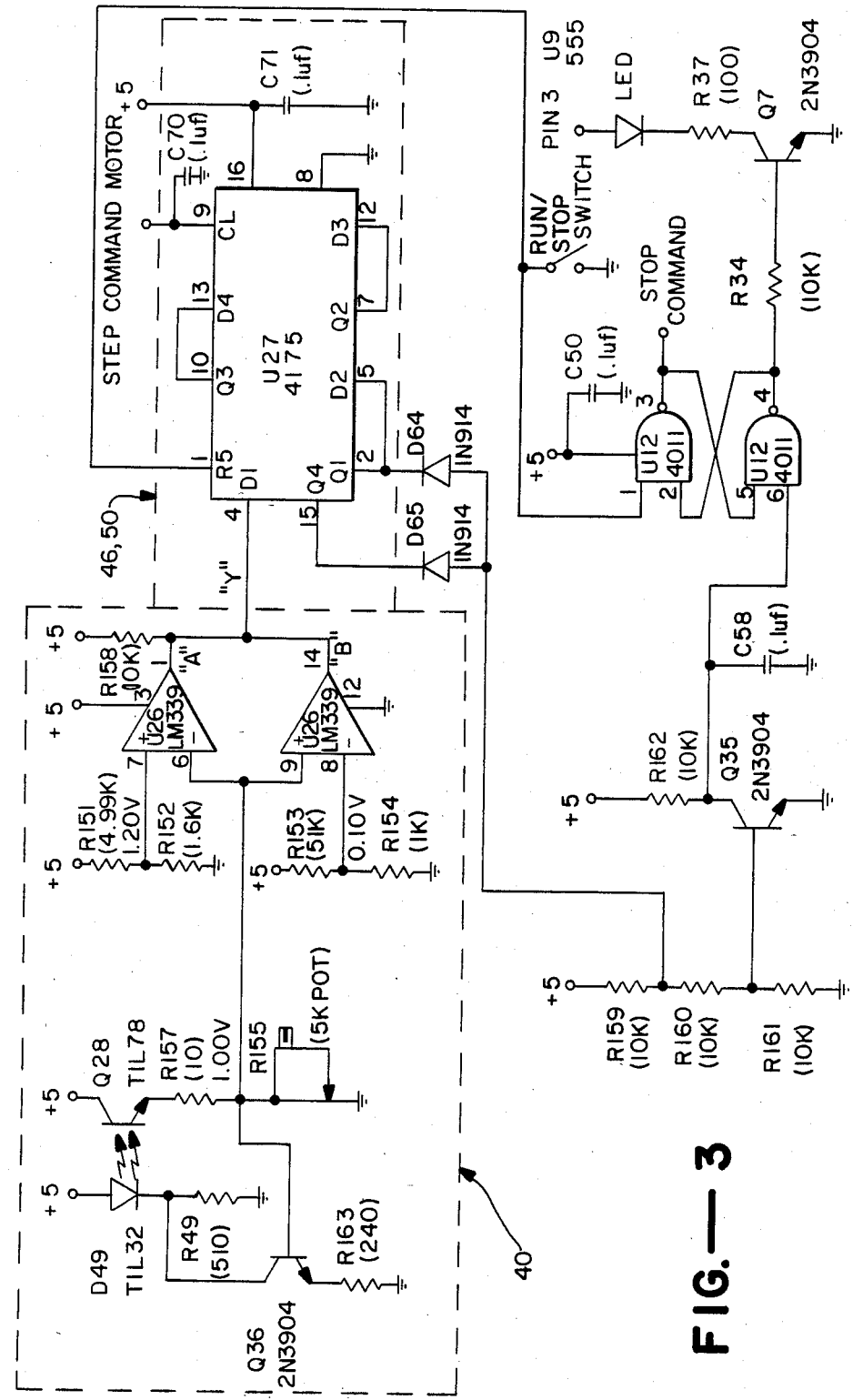
FIG.—3

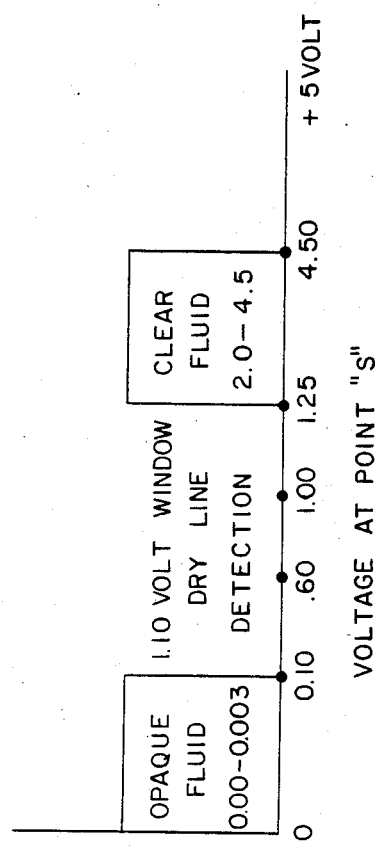
FIG.—4
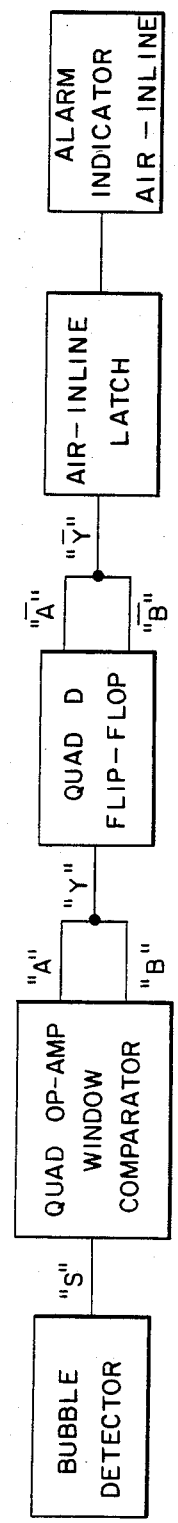
FIG.—5

AIR BUBBLE DETECTING AND DISCRIMINATING CIRCUIT ARRANGEMENT AND METHOD

The present invention relates generally to techniques for detecting air bubbles in fluid flowing through a continuous length of tubing and more particularly to a specific air bubble detecting circuit arrangement especially suitable for use with a peristaltic infusion pump assembly of the type described in U.S. Pat. No. 4,187,057 (Xanthopoulos).

The peristaltic infusion pump assembly described in the U.S. Patent just recited (hereinafter referred to as the Xanthopoulous patent) is one which includes a peristaltic infusion pump in combination with a disposable cassette. The cassette includes a cassette body which supports a continuous length of tubing is adapted for connection at one end to a supply of fluid and at its opposite end to a patient. The peristaltic infusion pump includes a variable speed stepping motor and a peristaltic pump head which is driven by the motor and which acts on the tubing for peristaltically pumping fluid therethrough at a flow rate proportionate to the speed of the motor. The overall assembly includes means for varying the flow rate by varying the speed of the stepping motor.

It is important that all infusion pumps including the one described immediately above include some means of detecting for air bubbles within the fluid being pumped and for simultaneously stopping the flow of fluid and setting off an alarm in the event a bubble sufficiently large to cause damage is detected. In this regard, applicant has found that microbubbles that is, those air bubbles which are less than 0.04 cm in volume (hereinafter referred to as nuisance bubbles) need not be detected since their presence within the fluid stream is harmless. Moreover, they are so often present in the fluid stream that to stop the infusion pump in response to their presence would be impractical. On the other hand, to eliminate these microbubbles from the stream would likewise be impractical.

It is not only important to detect for air bubbles of significant size in the fluid stream of a peristaltic infusion pump assembly, but it is also desirable to do this with complete reliability regardless of the flow rate of the fluid and whether or not the flow rate is changed at any given time. In this regard it should be noted that a given air bubble within the fluid stream will flow at the same rate as the fluid and therefore it will flow faster if the flow rate of the fluid is increased and it will slow down in speed if the flow rate of the fluid is decreased. As a result, in order for a bubble detecting arrangement to distinguish between problem bubbles, that is, those which are at least 0.04 cc in volume from nuisance bubbles, it may have to take into account these changes in flow rate of the bubble itself. This is particularly true if the bubble detecting arrangement utilizes a single point of detection rather than multiple points and bases the size (volume) of the bubble on its length in the tubing (assuming the bubbles are as wide as the tubing).

As will be seen hereinafter, the bubble detecting arrangement of the present invention utilizes a single point of detection technique with tubing which is sufficiently small in diameter that any problem bubble therein is as wide as the inner diameter of the tubing itself which means that its length varies directly with its volume. For example, using tubing having an inner diameter of 0.117 inch as the standard (hereinafter referred to as standard tubing) the problem bubbles will be those which are at least 0.224 inch long and 0.117 inch in diameter (e.g., at least 0.04 cc in volume). For purposes of describing the present invention, hereinafter it will be assumed that standard tubing is being used and that problem bubbles are those equal to or greater in length than the one just recited. Of course, nuisance bubbles will be those shorter in length than 0.224 inch.

In view of the foregoing, it is an object of the present invention to provide an uncomplicated and yet reliable arrangement for detecting air bubbles within fluid flowing through a continuous tube and for distinguishing between nuisance and problem bubbles, regardless of the flow rate of the fluid and without requiring any modifications to the arrangement as a result of any change in the flow rate.

Another object of the present invention is to provide a bubble detecting and discriminating arrangement in combination with a peristaltic infusion pump assembly generally, and specifically in combination with the assembly disclosed in the Xanthopoulous patent recited above.

Still another object of the present invention is to provide a bubble detecting and discriminating arrangement which utilizes a single point of detection and which reliably distinguishes between nuisance and problem bubbles in fluid passing through a continuous length of tubing including specifically tubing having the inner diameter recited above, again regardless of any changes in the flow rate of the fluid passing through the tubing.

A further object of the present invention is to provide a bubble detecting and discriminating arrangement for use with a peristaltic infusion pump assembly which includes a motor for causing the fluid within its tubing to flow at a given rate and specifically an arrangement which utilizes the assembly motor in order to compensate for changes in the flow rate when discriminating between problem bubbles and nuisance bubbles.

As will be described in more detail hereinafter, the peristaltic infusion pump assembly disclosed herein including its air bubble detecting and discriminating arrangement utilizes the following components. First, means are provided including a continuous length of tubing adapted for connection at one end to a supply of fluid and at its opposite end to a patient, as in the assembly described in the Xanthopoulous patent. Means are also provided including a variable speed motor acting on the tubing for peristaltically pumping the fluid therethrough at a flow rate proportionate to the speed of the motor whereby any air bubbles in the fluid will move with the latter at the same flow rate. The bubble detecting and discriminating arrangement includes means for detecting the presence of all air bubbles including both nuisance and problem bubbles as they pass through a fixed point along their path of movement through the tubing. The arrangement also includes means utilizing the previously mentioned motor for distinguishing between detected bubbles of at least a predetermined size (e.g., the problem bubbles) from smaller bubbles (the nuisance bubbles), regardless of the flow rate of the fluid in order to produce an alarm signal if problem bubbles are detected.

The bubble detecting and discriminating arrangement just described briefly will be discussed in more detail hereinafter in conjunction with the drawings wherein:

FIG. 1 is a front elevational view of an overall peristaltic infusion pump assembly including a bubble detecting and discriminating arrangement designed in accordance with the present invention and disclosed herein;

FIG. 2 diagrammatically illustrates in block diagram the way in which the bubble detecting and discriminating arrangement illustrated in FIG. 1 operates generally;

FIG. 3 is a schematic illustration of the bubble detecting and discriminating arrangement of FIG. 1 designed in accordance with an actual working embodiment;

FIG. 4 diagrammatically depicts an operational feature of the arrangement illustrated in FIG. 3; and FIG. 5 is a block diagram of the schematic illustration of FIG. 3.

Turning now to the drawings wherein like components are designated by like reference numerals throughout the various figures, attention is first directed to FIG. 1 which illustrates a peristaltic infusion pump assembly 10 including a bubble detecting and discriminating arrangement generally indicated at 12. Arrangement 12 is designed in accordance with the present invention as described briefly above, and as will be described in more detail hereinafter. The infusion pump assembly 10, apart arrangement 12, may be of any known design which is compatible with the bubble detecting and discriminating arrangement. In an actual working embodiment of the present invention assembly 10, again apart from arrangement 12, may be identical to the peristaltic infusion pump assembly described in the previously recited Xanthopoulous U.S. Pat. No. 4,187,057 and therefore reference is made to this latter patent.

For purposes of describing the present invention, it is necessary to discuss only certain components of overall assembly 10 which is otherwise described in the Xanthopoulous patent. These components include the assembly's peristaltic infusion pump which is comprised of a pump head 14 supported on the front face 16 of an assembly housing 18 and a variable speed stepping motor 20 for driving the pump head 14 at different rates of speed corresponding to the intended flow rate of fluid to be pumped by the overall assembly. A disposable cassette generally indicated at 22 also forms part of the assembly and includes a cassette body 24 which contains a continuous length of transparent tubing 26, one end of which is adapted for connection to a supply of fluid generally indicated at 28, the other end of which is adapted for connection to the patient. As illustrated in FIG. 1, the cassette body 24 is supported by suitable means to the front face 16 of the assembly housing 18 in a way which causes the pump head 14 to engage a predetermined lengthwise section of tubing 26 so as to peristaltically pump fluid through the tubing as the pump head rotates in the direction of arrow 32.

The flow rate of fluid through the tubing 26 is directly proportionate to the speed of rotation of the pump head which, in turn, is directly proportionate to the speed of stepping motor 20. Therefore, it can be said that the flow rate of fluid through the tubing is directly proportionate to the speed of the stepping motor. The importance of this relationship will become apparent hereinafter. For the moment, it suffices to say that overall assembly 10 includes suitable actuating means (not shown) for varying the flow rate of fluid through the tubing by varying the speed of the stepping motor. All of the other components making up the overall assembly other than arrangement 12 may be found in the Xanthopoulous patent and/or U.S. Pat. No. 4,256,437 which is directed to a specific stepping motor and associated components forming part of an actual assembly of the type described in the Xanthopoulous patent. Therefore, reference is also made to this latter U.S. patent.

As its name indicates, arrangement 12 serves to detect any air bubbles in tubing 26 as fluid flows through the latter and, at the same time, it distinguishes between nuisance bubbles and problem bubbles for automatically turning the overall assembly off and producing an alarm, but only if problem bubbles are present. In the specific assembly illustrated in FIG. 1, tubing 26 has an inner diameter of 0.117 inch as discussed above, and a problem bubble is defined as one having a volume of 0.04 cc or larger which corresponds to the length of 0.224 inches and a diameter of 0.117 inches within the tubing. Any bubbles shorter than this lengthwise (but having the same diameter) is considered a nuisance bubble. While arrangement 12 will be described with these parameters in mind, and in fact, operates in the embodiment illustrated with these parameters in mind, it is to be understood that the arrangement could be readily modified such that air bubbles of different sizes would qualify as either problem or nuisance bubbles, regardless of the diameter of tubing 26.

Referring to FIG. 2, attention is now directed to the way in which bubble detecting and discriminating arrangement 12 functions in accordance with the present invention generally. To this end, a section of tubing 26 is shown diagrammatically along with a stream of fluid indicated by arrow 34 which is flowing at a fixed rate. This fluid includes an air bubble 36 which is flowing with it and which is shown as its forwardmost end just begins to cross a fixed point 38 along its path of movement. Overall arrangement 12 is shown including means generally indicated at 40 for producing a light beam 42 across and through tubing 26 at point 38 and means generally indicated at 44 for detecting the light beam after it has passed through the tubing. A bubble detection circuit 46 is connected to the output of means 44 and produces an output signal depending on the light level of beam 42 as detected by means 44. More specifically, if either clear or opaque fluid is present at point 38 within tubing 26, circuit 46 provides what may be referred to as a non-alarm initiating signal (for example, a low level signal in binary language). On the other hand, as soon as an air bubble, for example air bubble 36, first appears at point 38, circuit 46 produces an alarm initiating signal generally indicated at 48 (for example, a high signal). The signal continues at the output of circuit 46 for as long as it takes the air bubble to pass through point 38. In other words, the duration of signal 48 corresponds to the length of air bubble 36. At the same time, a delay circuit 50 is also connected to the output of means 44 and also to stepping motor 20 forming part of the peristaltic pump described previously. Circuit 50 remains inactive until a bubble is first detected at point 38. At that time, using stepping motor 20 as a clock, it counts out a predetermined number of steps of the motor and thereafter produces its own alarm initiating output signal 52 if bubble 36 has not by that time entirely passed through point 38. In other words, if signal 48 is still present at the end of the delay, signal 52 (for example a high signal) is produced and remains at the output of circuit 50 for the duration of signal 48. On the other hand, if bubble 36 has entirely passed point 38 before the predetermined number of counts made by circuit 50, no signal 52 will be produced and the arrangment will reset itself in preparation for the next air bubble. If both signals 48 and 52 are present together, this means that bubble 36 is at least as long as the delay provided by circuit 50, e.g., at least a predetermined length, and therefore at least a predetermined volume. These two signals are applied to an alarm circuit 54 which is designed to respond to the presence of both signals to produce a latched in alarm signal 56 which may be visual, audio or both and also a signal (not shown) for turning off overall assembly 10.

Having described the bubble detecting and discriminating arrangement 12 as illustrated in FIG. 2, attention is now directed to the specific way in which this arrangement distinguishes between nuisance and problem bubbles regardless of the flow rate of fluid 34 through tubing 26. For purposes of discussion, let it first be assumed that the fluid flow rate is at a specific, fixed level which requires bubble 36 to use 6 steps of motor 20 in order to pass entirely through point 38. Let it also be assumed that any nuisance bubble would be sufficiently short lengthwise to pass entirely through point 38 in three steps at that flow rate. Therefore, in order to discriminate between nuisance bubbles and larger problem bubbles, it is only necessary to set the delay in circuit 50 to, for example, four steps. Thus, as soon as bubble 36 reaches point 38, signal 48 will be produced at the output of bubble detection circuit 46. At the same time, circuit 50 using stepping motor 20 will begin to count the steps of the motor. At the end of four steps, signal 52 will be produced. Since it takes six steps of the stepping motor to cause bubble 36 to move entirely through point 38, the bubble will still be present at point 38 at the end of the delay of circuit 50 and signal 52 will be produced simultaneously with signal 48, thereby producing alarm signal 56. If the bubble just mentioned was only three steps long, signal 48 would not have been present at the end of the delay in circuit 50 and therefore signal 52 would not have been produced and thus no alarm signal would have resulted.

Now, using the same bubble 36, let it be assumed that the flow rate of fluid 34 is doubled. Under this condition, the bubble 36 moves through point 38 twice fast. However, it still takes six steps of the stepping motor which is rotating twice as fast since it is responsible for the flow rate of fluid. More specifically, in order to double the flow rate, the motor would have to be driven at twice the speed. As a result, circuit 50 counts off its four steps before producing signal 52 twice as fast as before and therefore both signals 48 and 52 appear together even though signal 48 is half as long as it was previously because of the increase in the speed of the bubble. As a result, alarm signal 56 is produced regardless of the change in speed of the air bubble. This procedure works exactly the same way if the flow rate is decreased. In other words, while a lower flow rate causes the air bubble 36 to take longer to pass through point 38, the delay in circuit 50 is longer since it takes a longer time to provide four steps of motor 20 under these circumstances. This reasoning also applies for nuisance bubbles, which, in the example provided, would be shorter than four steps of motor 20. While bubble detecting and discriminating arrangement 12 is especially suitable for use with a stepping motor, and particularly one forming part of the peristaltic pump used in an overall assembly of the type illustrated in FIG. 1, it is to be understood that the arrangement could be provided with any other type of motor used for pumping fluid through a continuous length of tubing. It is only necessary that the motor be such that its speed varies proportionately with the flow rate of fluid. A stepping motor is especially suitable since it can be used as a clock without additional components. If a continuous motor is used, it would be necessary to provide some clock type means synchronized with the motor in order to provide a clock output corresponding thereto.

Having described arrangement 12 as illustrated in FIG. 2, attention is now directed to an actual working circuit which includes the functions of means 40 and 44 and circuits 46, 50 and 54. This actual working circuit is illustrated in FIG. 3. As seen therein, means 40 is comprised of a photodiode D49 and resistor R49. Means 44 includes phototransistor Q28, two operational amplifiers U26 and their associated components within the dotted box indicated at 44. These additional components include a number of resistors as illustrated and a variable potentiometer R155. Circuits 46 and 50 are both provided by the 4175 quad D flip-flop designated as U27 and the associated capacitors C71, as will become apparent hereinafter. This flip-flop is interconnected to stepping motor 20 at pin 9, the stepping motor serving as a clock for the flip-flop. Finally, alarm circuit 54 is comprised of the remaining components illustrated in FIG. 3, that is, those not enclosed within a dotted box including specifically the diode D64 which is connected to the output of flip-flop U27 serving as the output of circuit 46 and the diode D65 connected to the output of flip-flop U27 serving as the output to delay circuit 50, as well as transistor Q35, gate circuits U12, the LED and transistor Q7 and its cooperating components.

The specific arrangement illustrated in FIG. 3 has been designed to discriminate between the previously defined nuisance air bubbles (those less than 0.04 cc) and larger problem bubbles in tubing having an inner diameter of 0.117 inch. Moreover, this arrangement is able to detect air bubbles whether the carrier fluid flowing through the tubing is clear or opaque. In addition, this circuit will specifically shut down the pumps operating mode and simultaneously trigger both visual and audible alarms when a "dry line" condition occurs that exceeds a nuisance bubble (e.g., one which is greater than 0.15 cc).

The photodiode D49 and its associated components making up means 40 serve to produce previously described beam 42. The phototransistor Q28 and the operational amplifiers U26 including their cooperating components serve as a window comparator in order to distinguish clear fluid from opaque fluid from a dry line (e.g., an air bubble). The quad D flip-flop U27 and its associated components serve to produce previously described signal 48 and previously described delay signal 52 at its output pins 2 and 15, respectively. The remaining circuitry serves to respond to the presence of signals 48 and 52 in order to produce the previously mentioned visual and audible alarms as well as initiating the shutdown of the pump motor 20.

Still referring to FIG. 3 it can be seen that photodiode D49 is driven by 7.5 to 23.0 MA continuous forward current. The 5k potentiometer R155 sets the gain of phototransistor Q28 at a typical 1 volt level (in the absence of tubing 26). A wide range adjustable potentiometer (R155) from 0.00 to 4.5 volts is used to permit the use of a maximum number of existing bubble detectors. The operational amplifiers U26 function as comparators and are set to detect air in the tubing at 0.30 to 1.00 volt when using either opaque or clear fluid. The 4175 quad D flip-flop is clocked by motor 20 through pin 9; as stated previously, this signal being inverted from the stepper motor driver.

Resistors R151 and R152 form a voltage divider network which set pin 7 of comparator U26 to 1.2 volts. Resistors R153 and R154 also serve as a voltage divider network which sets pin 8 of the comparator to 0.10 volts. Thus, the range from 0.10 volts to 1.20 volts is the dry line detection window. The voltage above 1.20 volts represents clear fluid amplified by transistor Q28 and the voltage below 0.10 volts represents opaque fluid. This is best illustrated in FIG. 4.

In addition to the foregoing and still referring to FIG. 3, the combination of transistor Q36 and resistor R163 is shown connected in circuit with the LED D49 and resistor R49. This combination serves as a booster to amplify the current through D49 in order to compensate for manufacturing tolerances and variations in the different components making up the overall circuit.

Let it now be assumed that tubing 26 is placed into its operating position between the photodiode D49 and photo-transistor Q28 and that clear liquid is present at the point therebetween (e.g., point 38 in FIG. 2). As a result, the voltage at point S (pins 6 and 9 of the comparator) will read between 2.0 and 4.5 volts which is higher than pin 7. Therefore, output pin 1 of the comparator pulls pin 4 of flip-flop U27 low. The output pin 2 and pin 15 of the flip-flop are therefore also low. As a result, transistor 35 will not turn on because the output at U27 is low, consequently pin 6 in latch U12 will remain high due to the "pull up" resistor 162 and transistor Q27 will remain non-conductive thereby producing no alarm. If the IV pump is operated with opaque fluid, point Y operates between 0.00 volts and 0.008 volts which is lower than 0.10 volts at pin 8 of the comparator. As a result, the output 14 of the comparator pulls pin 4 low again. Therefore, the output pins 2 and 15 remain low and transistor Q35 remains off which, in turn, means that the latch U12 does not activate the alarm by causing transistor Q7 to conduct.

From the foregoing it should be apparent that the window comparator (the two operational amplifiers U26 and their associated components including photo-transistor Q28) work in complimentary relationship to one another. One of the operational amplifiers (e.g., the top one) sets the voltage at 1.2 volts for clear liquid which is the higher level voltage of the detection window and has the output at point A. The second operational amplifier (e.g., the lower one) puts the voltage at 0.10 volts for opaque fluid which is the lower level of the detection window and has the output at point B. The point S is the input of the window comparator which is set at 1 volt, typical without tubing at point 38. If a previously described cassette 22 is loaded into position with clear fluid within its tubing, point S should read 2.0 to 4.5 volts and if it carries opaque fluid it should read between 0.00 and 0.008 volts. Let it now be assumed that an air bubble is detected by the arrangement, and for the moment, assume that the air bubble is 0.1 cc in size (0.560 inch long by 0.117 inch in diameter). As soon as this air bubble is detected, the voltage at point S will be changed to a value between 0.30 and 1.0 volts. This voltage is low compared to 1.2 volts and high compared to 0.10 volts. Therefore, both comparators at outputs A and B will go high, making point Y high. This high output is applied to the flip-flop which makes point $\overline{B}$ (pin 2) immediately go high. Point $\overline{A}$ (pin 15) goes high after a three step delay in the stepping motor. In other words, after the fourth step in the motor, point $\overline{A}$ goes high. As a result, the point $\overline{Y}$ on the opposite sides of diodes D64 and D65 turns transistor Q35 on which in turn pulls the latch U12 to ground, thereby activating the alarm through transistor Q7.

On the other hand, if instead of a 0.1 cc air bubble, the tubing includes a 0.04 cc air bubble (e.g. one which is 0.244 inch long by 0.117 inch in diameter) the voltage at point S will go to about 0.60 volts and automatically sets the point Y to a high value. This in turn causes the $\overline{B}$ signal to go high. However, this size bubble will have passed entirely through the detecting window before pin 15 ($\overline{A}$) of the flip-flop has a chance to go high and therefore transistor Q35 will not turn on. Instead, the clear fluid and/or opaque fluid again enters the detecting window and resets the circuitry.

The overall description of the actual working circuitry illustrated in FIG. 3 is best illustrated in block diagram in FIG. 5. This block diagram should be self-explanatory in view of the foregoing and FIG. 3. Also, while FIG. 3 has been shown with actual circuit values (in parentheses), these values are provided for exemplary purposes only and are not intended to limit the present invention.

What is claimed is:

1. A peristaltic infusion pump, assembly, comprising:
   (a) means including a continuous length of tubing adapted for connection at one end to a supply of fluid and at its opposite end to a patient;
   (b) means including a variable speed motor acting on said tubing for peristaltically pumping said fluid therethrough at a flow rate proportionate to the speed of said motor, whereby any air bubbles in said fluid will move with the latter at the same flow rate;
   (c) means for detecting the presence of said air bubbles, if any, as they pass through a fixed point along the path of movement through said tubing, said detecting means being capable of producing a first signal in response to the presence of an air bubble at said fixed point and for the duration that the detected bubble passes through said point, the length of said first signal corresponding to the length of the detected bubble; and
   (d) means including said motor responsive to said detecting means for distinguishing between detected bubbles of at least a predetermined size which can cause problems from smaller nuisance bubbles which do not, regradless of the flow rate of the fluid, said distinguishing means including means for producing an alarm signal only if problem bubbles are detected, said distinguishing means being capable of producing a second signal for a predetermined period of time after initiation of said first signal, said second period of time being inversely proportionate to the speed of said motor, and said distinguishing means being capable of producing said alarm signal only during the presence of both said first and second signals, said time delay distinguishing between the larger problem bubbles and the smaller nuisance bubbles regardless of the flow rate of the fluid and bubbles.

2. An assembly according to claim 1 wherein said detecting means includes means for detecting air bubbles in either clear or opaque fluid without requiring any modification thereof.

3. In an infusion pump or like apparatus in which a liquid is caused to flow in a continuous stream through a continuous length of tubing by means of a motor such that the flow rate of the liquid is directly proportionate to the speed of said motor, an assembly for detecting air bubbles in said liquid stream and for distinguishing between problem bubbles of at least a predetermined size from smaller nuisance bubbles regardless of the flow rate of the stream, said assembly comprising:

(a) means for detecting the presence of air bubbles regardless of their size, as they pass through a fixed point along their path of movement through said tubing, said detecting means including means for producing a first signal in immediate response to the presence of an air bubble at said fixed point and for the duration that the detected bubble passes through said point, whereby the length of said first signal corresponds to the length of the detected bubble;

(b) means using said motor as a timing clock for producing a second signal a predetermined period of time after initiation of said first signal and for the duration of the latter, said period of time being inversely proportionate to the speed of said motor; and (c) means for producing an alarm signal in response to the simultaneous presence of said first and second signals, whereby said delay in the production of said second signal after the production of said first signal distinguishes between problem bubbles and smaller nuisance bubbles, regardless of the flow rate of fluid and bubbles through said tubing.

4. An assembly according to claim 3 wherein said motor is a stepping motor and wherein said second signal is produced a predetermined, fixed number of steps of stepping motor after initiation of said first signal.

5. A peristaltic infusion pump assembly, comprising:

(a) means including a continuous length of tubing adapted for connection at one end to a supply of fluid and at its opposite end to a patient;

(b) means including a variable speed motor acting on said tubing for peristaltically pumping said fluid therethrough at a flow rate proportionate to the speed of said motor, whereby any air bubbles in said fluid will move with the latter at the same flow rate, wherein said motor is a stepping motor;

(c) means for detecting the presence of said air bubbles, if any, as they pass through a fixed point along the path of movement through said tubing wherein said detecting means produces a first signal in response to the presence of an air bubble at said fixed point and for the duration that the detected bubble passes through said point, whereby the length of said first signal corresponds to the length of the detected bubble; and (d) means including said motor responsive to said detecting means for distinguishing between detected bubbles of at least a predetermined size which can cause problems from smaller nuisance bubbles which do not, regardless of the flow rate of the fluid, said distinguishing means including means for producing an alarm signal only if problem bubbles are detected, wherein said distinguishing means produces a second signal a predetermined period of time after initiation of said first signal, said period of time being inersely proportionate to the speed of said motor, and wherein said distinguishing means produces said alarm signal only during the presence of both said first and second signals, whereby said time delay distinguishes between the larger problem bubbles and the smaller nuisance bubbles regardless of the flow rate of the fluid and bubbles, said second signal being produced by a predetermined, fixed number of steps of said stepping motor after initiation of said first signal.

6. A peristaltic infusion pump assembly comprising:

(a) means including a continuous length of tubing adapted for connection at one end to a supply of fluid and at its opposite end to a patient;

(b) means including a variable speed stepping motor and a peristaltic pump head driven by said motor, said head acting on said tubing for peristaltically pumping said fluid therethrough at a flow rate proportionate to the speed of said stepping motor, whereby any air bubbles or dry sections in said tubing will move with said fluid at the same flow rate as the latter;

(c) means for detecting the presence of said air bubbles or dry sections, if any, as they pass through a fixed point along their path of movement through said tubing, said detecting means including means for producing a first electrical signal in response to the immediate presence of an air bubble or dry section at said first point and for the duration that the detected bubble or dry section passes through said point, whereby the length of said first signal corresponds to the length of said detected bubble or dry section;

(d) means for producing a second signal during a predetermined, fixed number of steps of said stepping motor after initiation of said first signal; and (e) means for producing an alarm signal only in response to the presence of both said first and second signals, whereby an alarm signal is produced upon detection of air bubbles of at least a predetermined size regardless of the flow rate of the fluid and bubbles through the tubing.

7. An assembly according to claim 6 wherein said detecting means includes a photoelectric arrangement located adjacent said tubing at said fixed point for directing a predetermined amount of light through the tubing on one side thereof and for detecting any light passing through the tubing on the other side thereof, said detecting means also including electric circuit means responsive to the amount of detected light passing through said tubing for distinguishing between clear fluid at said fixed point, opaque fluid at said fixed point, or no fluid at said fixed point within said tubing and for producing said first signal only if no fluid is at said fixed point and whereby said detecting means requires no modification for detecting air bubbles in either clear or opaque fluid.

8. A method of detecting air bubbles of at least a predetermined size from smaller bubbles in a peristaltic infusion pump or like apparatus in which a liquid is caused to flow in a continuous stream through a tube by means of a motor such that the flow rate of said fluid is directly proportionate to the speed of said motor, said method comprising the steps of:

(a) detecting the presence of said air bubbles, if any, as they pass through a fixed point along their path of movement through said tubing and producing a first signal as soon as an air bubble is detected at said point and for the duration that the detected bubble passes through said point whereby the length of said first signal corresponds to the length of the detected bubble;

(b) using said motor as a clock, producing a second signal a predetermined period of time after initiation of said first signal and for the duration of the latter, said period of time being inversely proportionate to the speed of said motor and therefore inversely proportionate to the flow rate of said fluid; and (c) producing an alarm signal in response to the simultaneous presence of said first and second signals, whereby said delay in the production of said second signal after production of said first signal distinguished between larger problem air bubbles and smaller nuisance air bubbles, regardless of the flow rate of fluid and bubbles through said tubing.

* * * * *